(12) United States Patent
Chinn

(10) Patent No.: US 7,524,288 B2
(45) Date of Patent: Apr. 28, 2009

(54) HOLDER FOR A HIGH INTENSITY FOCUSED ULTRASOUND PROBE

(76) Inventor: Douglas O. Chinn, 85 N. First Ave., #101, Arcadia, CA (US) 91006

( * ) Notice: Subject to any disclaimer, the term of this patent is extended or adjusted under 35 U.S.C. 154(b) by 629 days.

(21) Appl. No.: 11/062,218

(22) Filed: Feb. 22, 2005

(65) Prior Publication Data

US 2006/0241441 A1    Oct. 26, 2006

(51) Int. Cl.
*A61B 8/00* (2006.01)
(52) U.S. Cl. .................................................. 600/439
(58) Field of Classification Search ......... 600/437–439, 600/449, 459, 462–464, 1–8; 606/1, 2, 130; 396/421–422, 428
See application file for complete search history.

(56) References Cited

U.S. PATENT DOCUMENTS

| | | | | |
|---|---|---|---|---|
| 4,866,998 A * | 9/1989 | Stewart et al. | ............. | 73/866.5 |
| 5,444,507 A * | 8/1995 | Palmer | ................... | 396/421 |
| 5,673,696 A * | 10/1997 | Bidwell et al. | ............. | 600/437 |
| 5,871,448 A * | 2/1999 | Ellard | ................... | 600/459 |
| 5,931,786 A * | 8/1999 | Whitmore et al. | .......... | 600/459 |
| 5,957,935 A * | 9/1999 | Brown et al. | ................ | 606/130 |
| 6,036,649 A * | 3/2000 | Yuasa | ......................... | 600/462 |
| 6,042,277 A * | 3/2000 | Errington | .................... | 396/419 |
| 6,206,832 B1 * | 3/2001 | Downey et al. | ............. | 600/439 |
| 6,261,231 B1 * | 7/2001 | Damphousse et al. | ....... | 600/437 |
| 6,311,084 B1 * | 10/2001 | Cormack et al. | ............ | 600/411 |
| 6,398,711 B1 * | 6/2002 | Green et al. | ................... | 600/7 |
| 6,540,656 B2 * | 4/2003 | Fontayne et al. | ............... | 600/7 |
| 6,554,759 B2 * | 4/2003 | Fontayne et al. | ............... | 600/7 |
| 6,575,890 B2 * | 6/2003 | Kaplan et al. | ................... | 600/7 |
| 6,629,960 B2 * | 10/2003 | Fontayne | ................... | 604/240 |
| 6,659,956 B2 * | 12/2003 | Barzell et al. | ................ | 600/461 |
| 6,663,299 B1 * | 12/2003 | Shupak | ....................... | 396/422 |
| 7,232,265 B1 * | 6/2007 | Price | ........................... | 396/428 |
| 2002/0038117 A1 * | 3/2002 | Tokita et al. | .................. | 606/1 |
| 2002/0123689 A1 * | 9/2002 | Furia | ........................... | 600/461 |
| 2002/0143229 A1 * | 10/2002 | Green et al. | ................... | 600/7 |
| 2003/0012571 A1 * | 1/2003 | Nakatani | ..................... | 396/428 |
| 2003/0014039 A1 * | 1/2003 | Barzell et al. | ................... | 606/1 |
| 2003/0068098 A1 * | 4/2003 | Rondinelli et al. | .......... | 382/276 |
| 2003/0084732 A1 * | 5/2003 | Ehrlich et al. | ............ | 73/861.27 |

(Continued)

*Primary Examiner*—Long V Le
*Assistant Examiner*—Salieu M Abraham
(74) *Attorney, Agent, or Firm*—Morland C. Fischer

(57) ABSTRACT

A holder for a conventional high intensity focused ultrasound (HIFU) probe to be interfaced with a stepper atop a conventional tripod, or the like, to enable a physician/surgeon to image and visually inspect the rectal and prostate areas of a patient for signs of cancer and other abnormalities so that a treatment plan can be outlined and implemented. The probe holder includes a base, a pair of wall members detachably connected to one another at the front end of the base, and a pair of stand members detachably connected to one another at the rear end of the base. A first opening is formed between the pair of wall members to enclose and reliably support the proximal end of the probe. A second opening is formed between the pair of stand members to enclose and reliably support the distal end of the probe. A continuous cable passageway is established at the rear end of the base and past the lower stand member to permit the power cable to the probe to rotate freely in the event that the probe is correspondingly rotated relative to the base.

13 Claims, 3 Drawing Sheets

U.S. PATENT DOCUMENTS

2003/0153850 A1* 8/2003 Davis et al. .................. 601/2
2003/0192224 A1* 10/2003 Kirk ........................... 42/124
2004/0015080 A1* 1/2004 Kelly et al. ................ 600/437
2004/0143188 A1* 7/2004 Barzell et al. .............. 600/439
2005/0261572 A1* 11/2005 Babaliaros et al. ......... 600/415

* cited by examiner

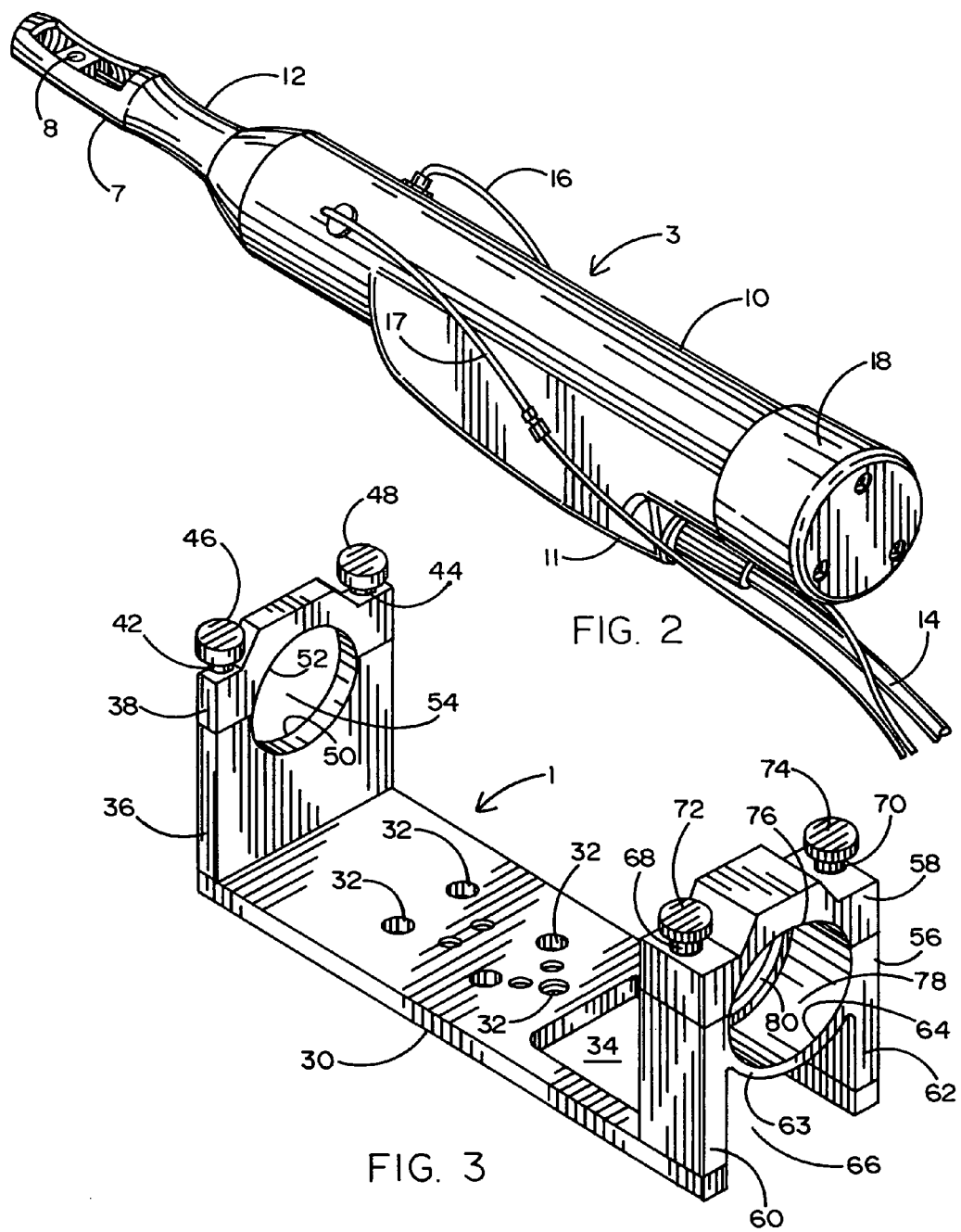

HOLDER FOR A HIGH INTENSITY FOCUSED ULTRASOUND PROBE

BACKGROUND OF THE INVENTION

1. Field of the Invention

This invention relates to a holder for a conventional high intensity focused ultrasound (HIFU) probe that is interfaced with a stepper atop a conventional tripod. The probe holder reliably and securely retains and supports the ultrasonic probe to be positioned relative to a patient in order to enable a physician/surgeon to image and visually examine the rectal and prostate areas for signs of cancer or other abnormalities so that a treatment plan can be outlined and then implemented.

2. Background Art

To enable a plan to be established prior to treating a patient for rectal or prostate disease, it is known for a physician/surgeon to first use a high intensity focused ultrasound probe to illuminate the targeted tissue area so that a visual image of the area is available at a video monitor. The high intensity focused ultrasound probe can then be used to simultaneously monitor and treat selected portions of the targeted tissue area as the treatment plan is implemented in accordance with information that is programmed into the probe. Should the high intensity focused ultrasound probe undesirably change its position relative to the target gland, the predetermined treatment plan will no longer be valid. As a consequence of such a position change, tissue areas in need of treatment could be missed or undertreated and/or the rectal wall or urinary sphincter could be damaged. Therefore, it is vital that the probe be capable of adjustment in any of the three orthogonally aligned planes, while unintended displacements which deviate from the treatment plan are avoided.

The conventional probe holders are typically table mounted devices having a swing arm and a relatively narrow collar that is carried by the swing arm to be coupled to the probe. Such a probe holder is characterized by several shortcomings. More particularly, the narrow collar is usually coupled to the proximal, relatively lightweight end of the probe. Because the distal end of the probe is heavier than the proximal end, the probe may not be adequately supported against undesirable tilting from a horizontal position. Moreover, the swing arm is typically long and narrow and, because it must extend to the proximal end of the probe, it has frequently proved to be unstable. Therefore, independent stabilization means have often been required to reinforce the support provided by the collar. What is more, the table mount end of the swing arm can be damaged as a result of many connect/disconnect cycles, which will not permit a reliable connection to the table. In this case, the swing arm and the probe are subject to unintended displacement during treatment of the patient. What is still more, the swing arm is commonly provided with an intermediate pivot which permits probe to be positioned through three orthogonal planes simultaneously. Accordingly, fine adjustments become difficult, such that when the pivot for the swing arm is loosened, the entire probe may be moved more than is intended or actually needed.

SUMMARY OF THE INVENTION

In general terms, disclosed herein is a holder for a conventional high intensity focused ultrasound (HIFU) probe of the type that has been commonly used as a scanning and treating tool to enable physicians/surgeons to gain a visual inspection of the rectal/prostate regions of a patient for signs of cancer or other abnormalities so that a treatment plan can be outlined and then implemented. The high intensity focused ultrasound probe includes a transrectal transducer that is carried by an imaging head at the proximal end thereof. After its insertion through the anus of a patient, the transrectal transducer is adapted to illuminate the patient's rectum and prostate regions and generate a visual image thereof to be displayed on a remote video monitor. Power to the probe is supplied via a power cable that extends to a suitable source of power. Located at the distal end of the probe is a cylindrical end cap that can be removed to permit access to the ultrasonic imaging and power regulating electronics.

The high intensity focused ultrasound probe holder includes an elongated base. Mounting holes are formed through the base to receive fasteners by which to enable the probe holder to be attached to a conventional stepper that is seated atop a tripod, or the like. Located at the front of the base are lower and upper wall members that are disposed one above the other. The upper wall member is detachably connected to the lower wall member by means of removable fasteners. In the connected relationship, a circular opening is formed through the lower and upper wall members so as to enclose and securely retain the proximal end of the probe at a location rearwardly of the imaging head and the transrectal transducer that is carried thereby. Located at the rear of the base of the probe holder are lower and upper stand members that are disposed one above the other. The upper stand member is detachably connected to the lower stand member by means of removable fasteners. In the connected relationship, an opening is formed through the lower and upper stand members to enclose and securely retain the cylindrical end cap at the distal end of the high intensity focused ultrasound probe.

The lower stand member is affixed to the rear of the base of the probe holder by way of a pair of legs that are separated from one another to create a cable space therebetween. An open window is formed in the rear of the base so as to be coextensive with the cable space. The open window and the cable space at the rear of the base cooperate with one another to establish a continuous passageway through which to receive the power cable from the high frequency ultrasonic probe. When it is desirable to rotate the probe relative to the probe holder during an examination or treatment of the patient, the upper wall member is loosened or removed from the lower wall member at the front of the base of the probe holder, and the upper stand member is loosened or removed from the lower stand member at the rear of the base. The coextensive alignment of the open window and the cable space at the rear of the base permits the unimpeded rotational displacement of the power cable during a corresponding rotation of the high intensity focused ultrasound probe over the base of the probe holder.

BRIEF DESCRIPTION OF THE DRAWINGS

FIG. 2 shows details of one high intensity focused ultrasound probe that is suitable to be retained and positioned by the probe holder in the manner shown in FIG. 1;

FIG. 3 is a perspective view of the probe holder shown in FIG. 1 according to the preferred embodiment;

DESCRIPTION OF THE PREFERRED EMBODIMENT

Figure 1:
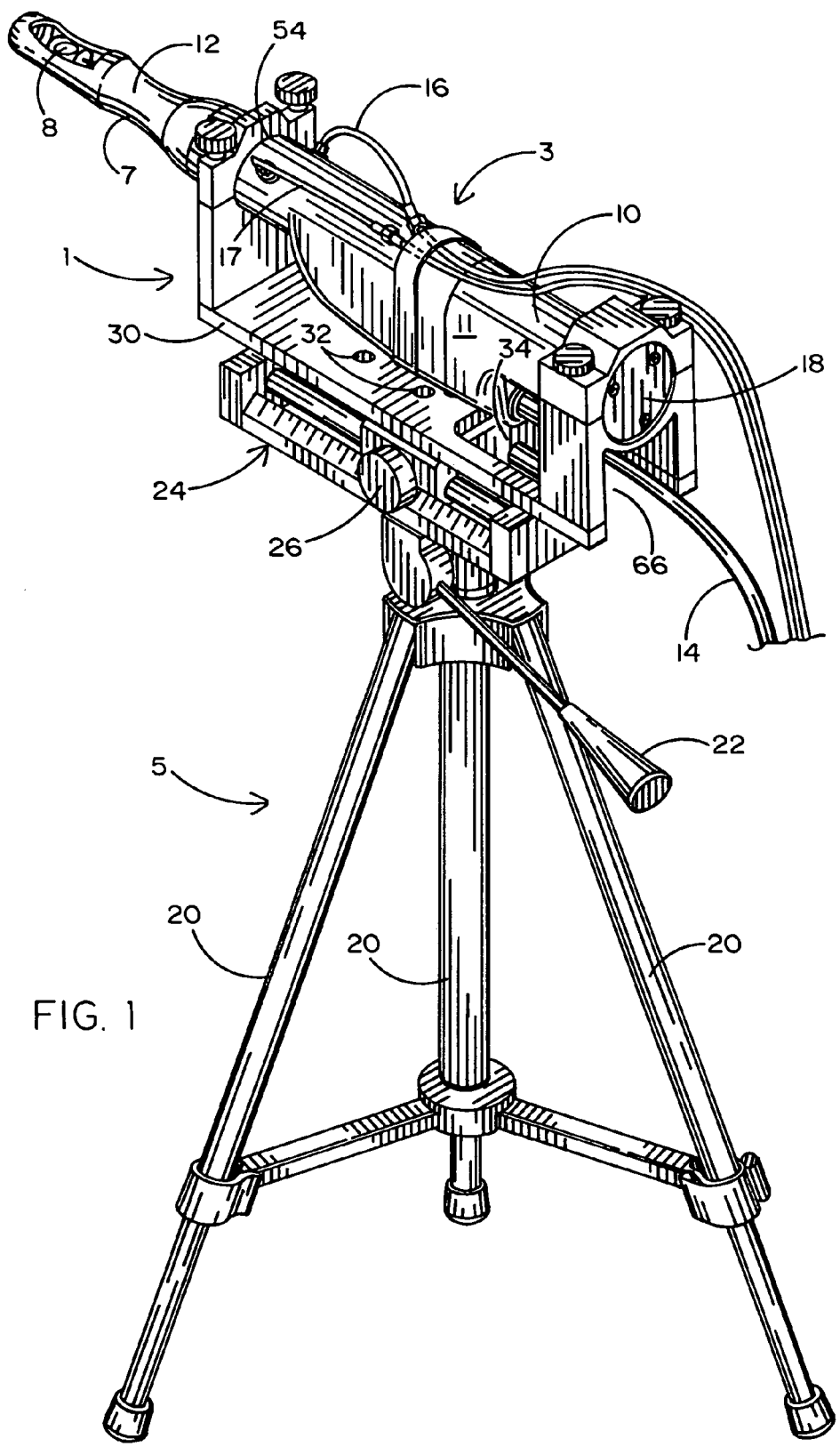
FIG. 1 illustrates the probe holder according to a preferred embodiment of this invention interfaced with a stepper and a high intensity focused ultrasound probe atop a tripod so that the probe can be securely retained and reliably positioned relative to a patient about to undergo a rectal/prostate examination or treatment.

A preferred embodiment of a holder 1 for a high intensity focused ultrasound (HIFU) probe 3 is now described while referring to the drawings. As will be disclosed in greater detail hereinafter, the probe holder 1 has particular application for reliably and securely supporting and retaining a commercially available high intensity focused ultrasound probe 3 of the kind that is commonly used as a monitoring and treating tool for enabling a physician/surgeon to conduct a rectal/prostate examination and visual inspection of a patient prior to and during a prescribed treatment when the probe 3 focuses high intensity ultrasound energy for heating the tissue in need of treatment. As will also be disclosed, the probe holder 1 is attached to the top of a tripod 5 to enable the probe 3 to be selectively positioned relative to the patient to be examined and treated.

Referring initially to FIGS. 1 and 2, details are now provided of the high intensity focused ultrasound probe 3 to be supported and retained by the probe holder 1 of this invention so that undesirable movements of the probe can be avoided during treatment. Inasmuch as the probe 3 shown in FIGS. 1 and 2 is generally known and forms no part of my improvement, only a brief description thereof will be provided below. In this regard, one commercially available high intensity focused ultrasound probe 3 which is suitable to be supported by the probe holder 1 is manufactured by Focus Surgery. Located at the proximal end of the probe 3 is an imaging head 7. Imaging head 7 carries a transrectal transducer 8 that is adapted to emit and receive incident and reflected high frequency ultrasonic energy so that a target tissue area in need of treatment may be illuminated and an image thereof captured. The transrectal transducer 8 is also adapted to heat the gland to be treated. The imaging head 7 is moved inwardly of the patient's anus to enable the transrectal transducer 8 to make an ultrasonic scan of the rectum and prostate during evaluation and to focus a high intensity energy spot during treatment.

Located opposite the imaging head 7 is a tubular main body 10 of the probe 3. The main body 10 houses the electronics that cooperate with the transrectal transducer 8 to enable the probe 3 to make the evaluation and treatment scans and to generate the high frequency energy necessary for heating the tissue to be treated. Extending downwardly from the main body 10 is an under-belly 11 in which the electronics of the probe 3 is located. A short neck 12 runs between the imaging head 7 and the main body 10 of the probe 3. A power cable 14 extends from a source of electrical power (not shown) to the under-belly 11 of main body 10 in order to provide power to the electronics located therein. Inlet and outlet lines 16 and 17 circulate a coolant through the body 10 of the probe 3 to minimize the adverse effects of heat.

In operation, imaging information collected by the transrectal transducer 8 at the imaging head 7 is transmitted to and displayed on a conventional video monitor (also not shown) to enable the physician/surgeon to visually scan the rectal and prostate regions of the patient in order to image and capture signs of cancer and other abnormalities. The transducer 8 also monitors the progress of the treatment plan that is implemented by the probe 3. A cylindrical end cap 18 (best shown in FIG. 2) is detachably connected to the main body 10 at the distal end of probe 3 to enable access to and servicing of the electronics thereof.

The tripod 5 upon which the probe holder 1 is seated is best shown in FIG. 1. Like the high intensity focused ultrasound probe 3, the tripod 5 is also a commercially available device and forms no part of my improvement. Therefore, only a brief description of tripod 5 will be provided below. A tripod 5 which is suitable to support the probe holder 1 may be a well known stand of the kind that is typically used to steady and elevate a camera. However, it is to be understood that the ultrasonic probe holder of this invention can be elevated by any other suitable stand. The tripod 5 includes a plurality of (three) telescoping legs 20 having variable lengths to adjust the elevation of the ultrasonic probe 3 and a control arm 22 that can be manipulated to cause the probe 3 to be tilted to adjust the angle of inspection or treatment. A conventional stepper 24 having a rotatable control knob 26 is attached to the top of tripod 5 to enable the physician to make fine horizontal position adjustments to the probe 3.

Figure 4:
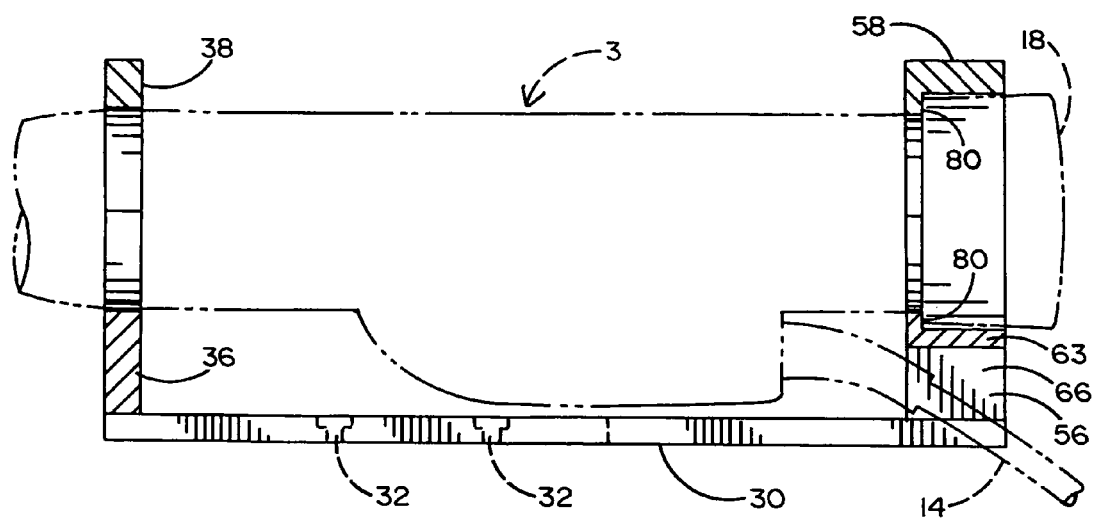
FIG. 4 is a side view of the probe holder of FIG. 3 with the high intensity focused ultrasound probe and its power cable shown in broken, phantom lines.
Figure 5:
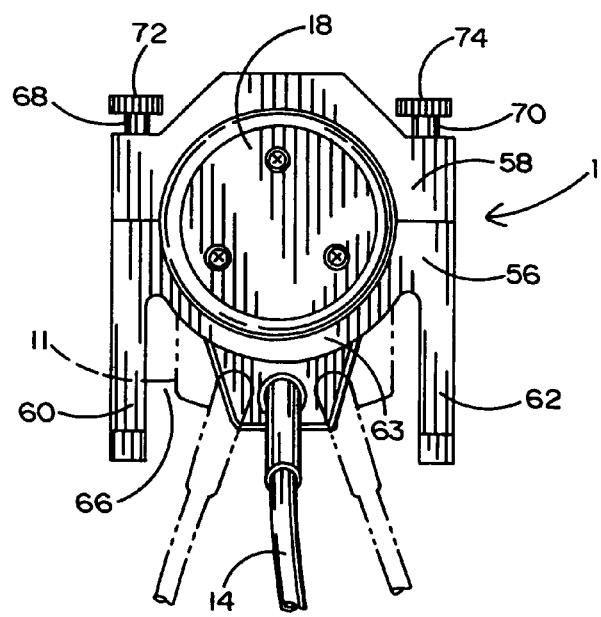
FIG. 5 is an end view of the probe holder of FIG. 3 to illustrate the ability of the power cable to rotate, without interference, as the high intensity focused ultrasound probe is correspondingly rotated relative to the probe holder.

Details of the probe holder 1 for reliably and securely supporting the high intensity focused ultrasound probe 3 are now disclosed while referring concurrently to FIGS. 3-5 of the drawings. The probe holder 1 includes a rectangular base 30 that is long enough to lie below the under-belly 11 of probe 3. The rectangular base 30 has an array of mounting holes 32 formed therein in which to receive suitable fasteners (not shown) whereby the base 30 can be detachably connected to any one of a variety of commercially available steppers, such as those manufactured by Amertek or Barzell Whitmore. As indicated previously when referring to FIG. 1, the stepper 24 is attached to the top of the tripod 5. Therefore, the probe holder 1 will sit atop the tripod 5 after the base 30 of holder 1 is connected to the stepper 24, whereby the high intensity focused ultrasound probe 3 will be capable of movement in each of the three orthogonally aligned planes.

In order to enable the imaging head 7 of probe 3 to be introduced through the patient's anus, the base 30 of probe holder 1 should be shorter than the tubular main body 10 of the probe 3 (best illustrated in FIG. 4). In this case, the neck 12 and imaging head 7 which carries the transrectal transducer 8 will project past the front of the probe holder 1 to be positioned relative to the patient who will undergo a rectal/prostate examination and treatment. As an important aspect of my improvement, an open window 34 (best shown in FIG. 3) is formed in the rear of base 30. The advantage of the open window 34 at the rear of base 30 will soon be disclosed.

Located at and standing vertically upright from the front of the base 30 of probe holder 1 are lower and upper wall members 36 and 38. The lower wall member 36 is affixed to the front of the base 30 by suitable (e.g., screw threaded) fasteners (not shown) that preferably project upwardly from the bottom of the base 30 for receipt at the bottom of the lower wall member 36. A downwardly turning semicircular opening 50 is formed in the top of the lower wall member 36. As illustrated in FIGS. 1 and 4, the opening 50 is sized and shaped to receive and cradle the bottom of the tubular main body 10 at the proximal end of the probe 3.

The upper wall member 38 is located above and detachably connected to the lower wall member 36 at the front of base 30. To enable the physician to easily separate the upper wall member 38 from the lower wall member 36, a pair of (e.g., screw threaded) fasteners 42 and 44 project downwardly from the top of upper wall member 38 for receipt at the top of lower wall member 36. A wide head 46 and 48 is connected to the top of each of the fasteners 42 and 44. When the physician/surgeon wishes to either raise or remove the upper wall member 38 from the lower wall member 36, the heads 46 and 48 are grasped and rotated to correspondingly rotate fasteners 42 and 44 out of engagement with the lower wall member 36. At this point, the upper wall member 38 is simply lifted up or off or rotated relative to the lower wall member 36.

An upwardly turning semicircular opening 52 is formed in the bottom of the upper wall member 38. As is also illustrated in FIGS. 1 and 4, the opening 52 is sized and shaped to receive and surround the top of the tubular main body 10 at the proximal end of the probe 3. In the assembled probe holder configuration with the upper wall member 38 mounted on the lower wall member 36 by means of fasteners 42 and 44, the semicircular openings 52 and 50 of respective wall members 38 and 36 will be aligned one above the other to form a circular opening 54 (best shown in FIG. 3). Circular opening 54 is adapted to accommodate therewithin and enclose the tubular main body 10 at the proximal end of probe 3, such that the imaging head 7 and the transrectal transducer 8 that is carried thereby project outwardly and forwardly from opening 54 and past the front of the base 30 of the probe holder 1, as previously explained, in order to be introduced through the patient's anus.

Located at and standing vertically upright from the rear of the base 30 of the probe holder 1 are lower and upper stand members 56 and 58. The lower stand member 56 includes a pair of opposing legs 60 and 62. The legs 60 and 62 of lower stand member 56 are affixed to the rear of the base 30 by means of suitable (e.g., screw threaded) fasteners (not shown) that preferably project upwardly from the bottom of base 30 for receipt at the bottom of legs 60 and 62. A downwardly turning rim 63 having a semicircular shape runs between the opposing legs 60 and 62 to establish a semicircular opening 64 at the top of the lower stand member 56. Opening 64 is sized and shaped to receive and cradle the bottom of the cylindrical end cap 18 at the distal end of the probe 3.

Extending between the opposing legs 60 and 62 at the bottom of the lower stand member 56 and lying under the rim 63 is a cable space 66. It is important to note that the cable space 66 is coextensive to the open window 34 that is formed in the rear of the base 30 of probe holder 1. By virtue of the coextensive alignment of the window 34 and the cable space 66, and as is best shown in FIG. 1, a continuous horizontal and vertical passageway is established through which to receive the power cable 14 which runs from the under-belly 11 of the tubular body 10 and rearwardly of the ultrasonic probe 3. In this same regard, and as is best shown in FIG. 5, the cable space 66 between the opposing legs 60 and 62 of the lower stand member 56 permits the unimpeded rotational displacement of the power cable 14 (represented by broken, phantom lines) should the probe 3 need to be rotated relative to the base 30 of probe holder 1 during examination or treatment of the patient.

The upper stand member 58 is located above and detachably connected to the lower stand member 56 at the rear of the base 30. To enable the physician/surgeon to easily separate the upper stand member 58 from the lower stand member 56, a pair of (e.g., screw threaded) fasteners 68 and 70 project downwardly from the top of upper stand member 58 for receipt at the top of the lower stand member 56. A wide head 72 and 74 is connected to the top of each of the fasteners 68 and 70. The pair of fasteners 42 and 44 for detachably connecting the upper wall member 38 to the lower wall member 36 at the front of the base 30 of probe holder 1 may be identical to the pair of fasteners 68 and 70 for detachably connecting the upper stand member 58 to the lower stand member 56 at the rear of the base 30.

When the physician/surgeon wishes to either raise or remove the upper stand member 58 from the lower stand member 56, the heads 72 and 74 are grasped and rotated to correspondingly rotate the fasteners 68 and 70 out of engagement with the lower stand member 56. At this point, the upper stand member 58 is simply lifted up or off or rotated relative to the lower stand member 56.

An upwardly turning semicircular opening 76 is formed in the bottom of the upper stand member 58. Opening 76 is sized and shaped to receive and surround the top of the cylindrical end cap 18 at the distal end of the probe 3. In the assembled probe holder configuration, with the upper stand member 58 mounted on the lower stand member 56 by means of fasteners 68 and 70, the semicircular openings 76 and 64 of respective stand members 58 and 56 will be aligned one above the other to form a circular opening 78 (best shown in FIG. 3). Circular opening 78 is adapted to accommodate therewithin and enclose the cylindrical end cap 18 at the distal end of the probe 3 (best shown in FIGS. 4 and 5).

A flange or lip 80 projects from each of the lower and upper stand members 56 and 58 so as to extend around the circular opening 78 therebetween (best shown in FIGS. 3 and 4) in which to receive the end cap 18 of the probe 3. In the assembled configuration of FIG. 4, the end cap 18 abuts the opposing flanges 80 so that the probe 3 can be rotated within the probe holder 1 but without accidentally moving into the patient's rectum. Although the flanges 80 are shown on one side of lower and upper support members 56 and 58, such flanges may also be formed on both sides thereof.

The probe holder 1 disclosed herein will reliably and securely retain and support the entire high intensity focused ultrasound probe 3 between the proximal and distal ends thereof for attachment to a stable floor stand (e.g., a tripod, or the like) in order to prevent an unintended displacement of the probe once it is positioned and moved relative to the patient to be evaluated and treated. Should the probe 3 need to be rotated within or removed from the probe holder 1, the upper wall and stand members 38 and 58 are either lifted up or separated from or rotated relative to the lower wall and stand members 36 and 56 that are located at opposite ends of the base 30 in the manner previously described. The coextensive horizontally extending open window 34 and vertically extending cable space 66 provide a long and tall passageway to enable the rotation or removal of the probe 3 without interference from the power cable 14.

I claim:
1. The combination, comprising:
a high intensity focused ultrasound probe having proximal and distal ends, an imaging head located at the proximal end, an ultrasonic transducer carried by said imaging head to illuminate a targeted tissue area of a patient to be treated so as to provide a visual image thereof, and a power cable to supply power to said probe; and
a probe holder to support and position said high intensity focused ultrasound probe relative to the patient, said probe holder including a base having front and rear ends, a first support fixedly connected to the front end of said base to be detachably connected to and in direct contact with the proximal end of said probe in order to fixedly hold said proximal end above said base such that the imaging head of said probe projects forwardly of said front end to be introduced to the patient, and a second support fixedly connected to the rear end of said base to be detachably connected to and in direct contact with the distal end of said probe, said first and second supports remaining stationary relative to one another.

2. The combination recited in claim 1, wherein said first support at the front end of the base of said probe holder includes a wall having an opening formed therein to receive and surround the proximal end of said high intensity focused ultrasound probe.

3. The combination recited in claim 2, wherein the wall of said first support includes a lower wall member and an upper wall member detachably connected to said lower wall member, said opening extending between said lower and upper wall members for receipt of the proximal end of said high intensity focused ultrasound probe therewithin.

4. The combination recited in claim 3, further comprising fasteners by which to detachably connect said upper wall member to said lower wall member at the front end of the base of said probe holder.

5. The combination recited in claim 1, wherein said second support at the rear end of the base of said probe holder includes a stand having an opening formed therein to receive and surround the distal end of said high intensity focused ultrasound probe.

6. The combination recited in claim 5, wherein the stand of said second support includes a lower stand member and an upper stand member detachably connected to said lower stand member, said opening extending between said lower and upper stand members for receipt of the distal end of said high intensity focused ultrasound probe therewithin.

7. The combination recited in claim 6, further comprising fasteners by which to detachably connect said upper stand member to said lower stand member at the rear end of said probe holder.

8. The combination recited in claim 6, further comprising a flange carried by at least one of said upper and lower stand members and extending around at least some of said opening therebetween to engage the distal end of said high intensity focused ultrasound probe and thereby permit said probe to rotate within said probe holder without sliding linearly through said opening.

9. The combination recited in claim 6, wherein said lower stand member includes a pair of legs that are separated from one another to create a cable space therebetween, the power cable of said high intensity focused ultrasound probe extending past and rotating laterally between said pair of legs when said high intensity focused ultrasound probe is correspondingly rotated relative to the base of said probe holder.

10. The combination recited in claim 9, wherein the rear end of the base of said probe holder has an open window formed therethrough, said open window through said base and said cable space between the pair of legs of said lower stand member cooperating with one another to establish a continuous passageway for the power cable of said high intensity focused ultrasound probe.

11. The combination recited in claim 1, wherein the base of said probe holder has a plurality of mounting holes formed therein and adapted to receive respective fasteners therethrough by which to removably attach said probe holder to an upright stand.

12. For a high intensity focused ultrasound probe having proximal and distal ends, an imaging head located at the proximal end, an ultrasonic transducer carried by said imaging head to illuminate a targeted tissue area of a patient to be treated so as to provide a visual image thereof, and a power cable to supply power to said probe, the improvement comprising:
a probe holder to support and position said high intensity focused ultrasound probe relative to the patient, said probe holder including a base having front and rear ends, a first support located at the front end of said base and having a first opening formed therein to surround and fixedly retain the proximal end of said probe such that the imaging head of said probe projects forwardly of said front end to be introduced to the patient, a second support fixedly connected to the rear end of said base and having a second opening formed therein to surround and fixedly retain the distal end of said probe, and a cable opening formed through said base between said first and second supports, said second support remaining stationary relative to said cable opening so as to enable the power cable of the probe to be received through said opening regardless of the position of said probe relative to said probe holder.

13. The improvement recited in claim 12, wherein the first support of said probe holder is fixedly connected to the front end of said base such that said first and second supports remain stationary relative to one another.

* * * * *